United States Patent
Normark et al.

(10) Patent No.: US 8,012,412 B2
(45) Date of Patent: Sep. 6, 2011

(54) METHOD AND DEVICE FOR PURIFYING AMBIENT AIR AND SURFACES

(75) Inventors: James Normark, Fall Branch, TN (US); Neal Morris, Greeneville, TN (US); Allen Johnston, Jonesborough, TN (US)

(73) Assignee: Vollara, LLC, Dallas, TX (US)

( * ) Notice: Subject to any disclaimer, the term of this patent is extended or adjusted under 35 U.S.C. 154(b) by 846 days.

(21) Appl. No.: 11/832,890

(22) Filed: Aug. 2, 2007

(65) Prior Publication Data
US 2009/0035176 A1 Feb. 5, 2009

(51) Int. Cl.
- *A61L 2/00* (2006.01)
- *A62B 7/08* (2006.01)
- *B01J 19/08* (2006.01)
- *G01N 23/00* (2006.01)
- *B03C 3/00* (2006.01)
- *B01D 46/00* (2006.01)
- *B01D 39/00* (2006.01)

(52) U.S. Cl. ........ 422/24; 422/1; 422/121; 422/186.04; 422/186.1; 422/186.3; 422/900; 250/455.11; 95/285; 95/57; 96/15; 96/224

(58) Field of Classification Search ................ 422/1, 25, 422/121, 186.04, 186.1, 186.3, 900; 250/455.11; 95/285, 57; 96/15, 224
See application file for complete search history.

(56) References Cited

U.S. PATENT DOCUMENTS

| | | | |
|---|---|---|---|
| 4,748,051 A | 5/1988 | Songer et al. | |
| 5,261,946 A | 11/1993 | Overby | |
| 5,933,702 A * | 8/1999 | Goswami | 422/186.3 |
| 6,632,771 B1 * | 10/2003 | Maekawa et al. | 502/239 |
| 6,730,265 B2 * | 5/2004 | Horton, III | 422/24 |
| 6,783,578 B2 | 8/2004 | Tillman, Jr. | |
| 6,828,273 B2 * | 12/2004 | Tanaka et al. | 502/263 |
| 6,902,603 B2 | 6/2005 | Wiser, III et al. | |
| D518,160 S | 3/2006 | Normark | |
| 7,166,259 B2 | 1/2007 | Beam et al. | |
| 2002/0081246 A1 * | 6/2002 | Tsukada et al. | 422/186.3 |
| 2005/0186124 A1 | 8/2005 | Fink et al. | |
| 2006/0266221 A1 | 11/2006 | Fink et al. | |

* cited by examiner

*Primary Examiner* — Jill Warden
*Assistant Examiner* — Monzer R Chorbaji
(74) *Attorney, Agent, or Firm* — Klemchuk Kubasta LLP; Darin M. Klemchuk; Shannon W. Bates (57) ABSTRACT

Described is an air and surface purifying device having a purifying cell structured for maximizing the realized photocatalytic reaction at a photocatalytic surface without using an additional ultraviolet bulb. The purifying cell positions at least three photocatalytic surfaces about a single ultraviolet bulb such that the photocatalytic surfaces substantially encompass the ultraviolet bulb and are saturated by ultraviolet light radiating from the ultraviolet bulb. Because the photocatalytic surfaces are saturated, the potential photocatalytic reaction at the photocatalytic surfaces is fully realized. Stated differently, the realized photocatalytic reaction is maximized. Because the purifying cell maximizes the realized photocatalytic reaction, the purifying cell maximizes the purifying capacity of the photocatalytic surface and, thus, the purifying cell itself.

32 Claims, 6 Drawing Sheets

METHOD AND DEVICE FOR PURIFYING AMBIENT AIR AND SURFACES

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

This invention pertains to a method and device for purifying ambient air and surfaces. More particularly, this invention pertains to a method and device for removing organic contaminants from ambient air and surfaces utilizing a photocatalytic reaction.

2. Description of the Related Art

Figure 1:
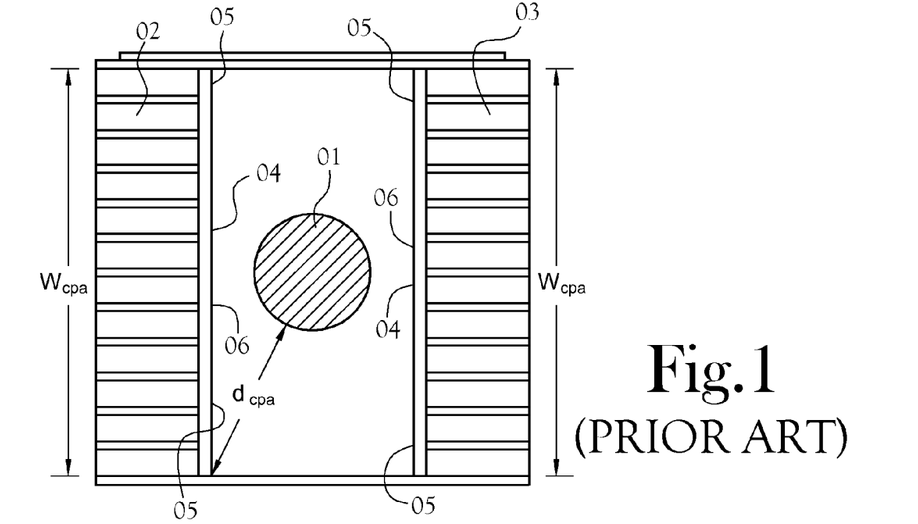
FIG. 1 illustrates a cross-sectional view of a conventional air purifying apparatus that is part of the prior art.

FIG. 1 illustrates a cross-sectional view of a conventional air purifying apparatus that is a part of the prior art. The conventional purifying apparatus includes an ultraviolet bulb 01, a first matrix 02, and a second matrix 03. Each of the first matrix 02 and the second matrix 03 includes a width $w_{cpa}$ and a photocatalytic surface 04 facing the ultraviolet bulb 01. When the ultraviolet bulb 01 radiates ultraviolet light, a photocatalytic reaction occurs at the photocatalytic surface 04 of the first matrix 02 and the second matrix 03. Air subjected to the photocatalytic reaction is oxidized and thus purified.

A conventional purifying apparatus is limited in that the potential photocatalytic reaction at the first matrix 02 and the second matrix 03 is not fully realized. More specifically, the positional relationship between the ultraviolet bulb 01 and each of the matrices is such that the distance $d_{cpa}$ between the ultraviolet bulb 01 and the outermost portions 05 of the photocatalytic surface 04 of each of the first matrix 02 and the second matrix 03 is large to the extent that ultraviolet light exposure at the outermost portions 05 of the photocatalytic surfaces 04 is not sufficient to saturate the photocatalytic surfaces 04. When the photocatalytic surface 04 is not saturated, the realized photocatalytic reaction is not maximized. Consequently, only the centermost portions 06 of the photocatalytic surfaces 04 are exposed to ultraviolet light sufficient to maximize the realized photocatalytic reaction. As a result, using a conventional purifying apparatus to generate a particular photocatalytic reaction requires more photocatalytic surface 04 than necessary. Stated differently, a portion of the photocatalytic surface 04 of a conventional purifying apparatus, and consequently potential photocatalytic reaction, is wasted.

Another conventional purifying apparatus addresses the above-discussed limitation by employing additional ultraviolet bulbs 01 along the width $w_{cpa}$ of the first matrix 02 and the second matrix 03 such that the outermost portions 05 of the photocatalytic surfaces 04 are exposed to sufficient ultraviolet light for maximum photocatalytic reaction. However, adding additional ultraviolet bulbs 01 increases the part count per apparatus, power consumption, and heat generation. Consequently, a device that maximizes the realized photocatalytic reaction at a given photocatalytic surface without increasing the radiated ultraviolet light is desired.

BRIEF SUMMARY OF THE INVENTION

In accordance with the various features of the present invention there is provided an air and surface purifying device having a purifying cell structured for maximizing the realized photocatalytic reaction at a photocatalytic surface without using an additional ultraviolet bulb. The purifying cell includes a single ultraviolet (UV) bulb and at least three matrices, each of the matrices having a photocatalytic surface. The matrices are positioned about the UV bulb such that the matrices substantially encompass the UV bulb and each photocatalytic surface is directed towards the UV bulb. The matrices are also positioned such that the distance between the outermost portions of each photocatalytic surface and the UV bulb is such that the entire photocatalytic surface of each of the matrices is saturated by the UV light radiated by the UV bulb. When the entire photocatalytic surface is saturated, the potential photocatalytic reaction at the photocatalytic surface is fully realized. Consequently, for a given combined photocatalytic surface area, the purifying cell maximizes the photocatalytic reaction.

The purifying device also includes a housing that receives the purifying cell. The housing draws ambient air into the housing, circulates the air through the purifying cell such that the air is subjected to the photocatalytic reaction, and then forces the air from the housing. When the air is subjected to the photocatalytic reaction, the air is oxidized such that organic contaminants are removed from the air to the extent the air is purified. Consequently, the purifying device purifies the ambient air. Because the purifying cell maximizes the realized photocatalytic reaction, it maximizes the purifying capacity of the purifying cell.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

The present invention provides an air and surface purifying device having a purifying cell structured for maximizing the realized photocatalytic reaction at a photocatalytic surface without using an additional ultraviolet bulb. The purifying cell positions at least three photocatalytic surfaces about a single ultraviolet bulb such that the photocatalytic surfaces substantially encompass the ultraviolet bulb and are saturated by ultraviolet light radiating from the ultraviolet bulb.

Because the photocatalytic surfaces are saturated, the potential photocatalytic reaction at the photocatalytic surfaces is fully realized. Stated differently, the realized photocatalytic reaction is maximized. Because the purifying cell maximizes the realized photocatalytic reaction, the purifying cell maximizes the purifying capacity of the photocatalytic surface and, thus, the purifying cell itself. One embodiment of the purifying device constructed in accordance with the various features of the present invention is illustrated generally at 10 in FIG. 2.

Figure 2:
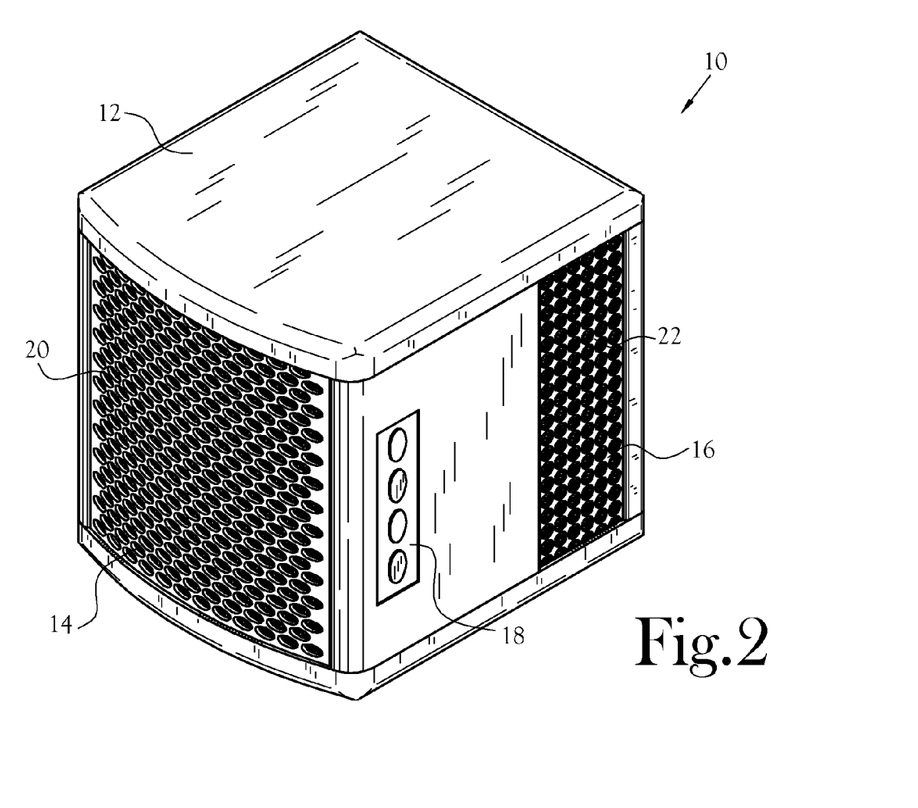
FIG. 2 illustrates one embodiment of the purifying device in accordance with the various features of the present invention.
Figure 3:
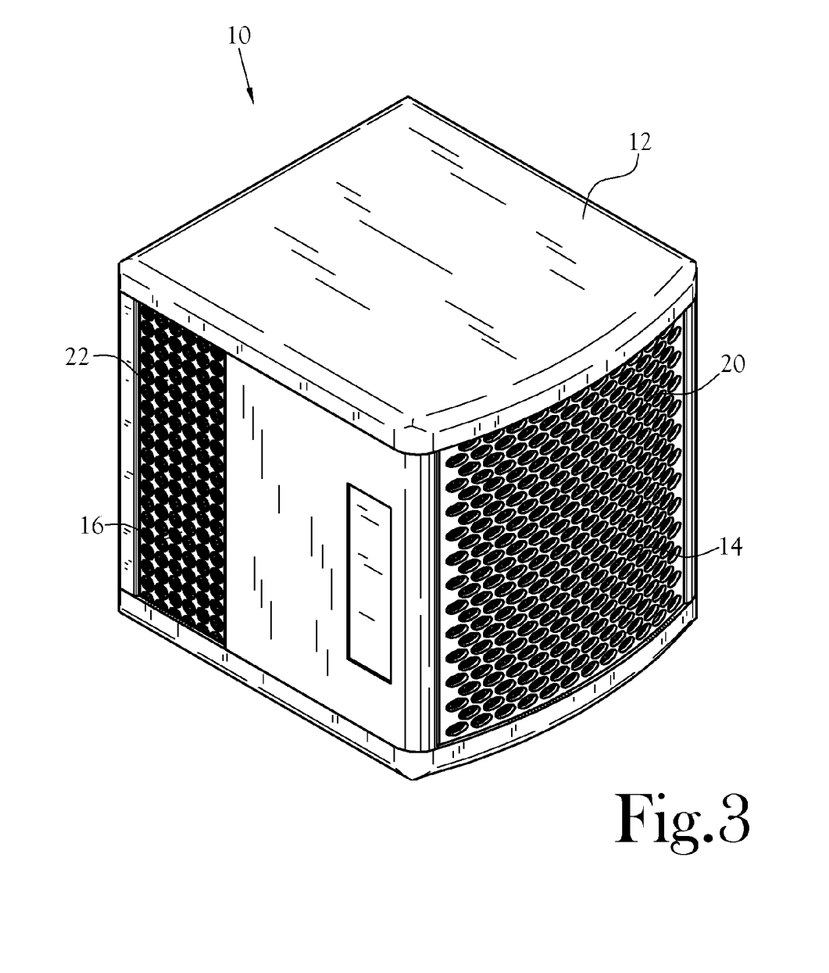
FIG. 3 illustrates an alternate view of the purifying device of FIG. 2.

The purifying device 10 of FIG. 2 includes a housing 12 that defines an air outlet 14 and an air inlet 16. In the illustrated embodiment, the housing 12 defines a front grill 20 at the air outlet 14 and a side grill 22 at the air inlet 16. Additionally, in the illustrated embodiment, the housing 12 defines an air inlet 16 and a side grill 22 at each side of the housing 12. (Consider FIG. 3). Those skilled in the art will recognize that the number and position of each of the air outlet 14 and the air inlet 16 can vary without departing from the scope or spirit of the present invention. The purifying device 10 draws air into the housing 12 by way of the air inlet 16 and forces air from the housing 12 by way of the air outlet 14 such that air is circulated through the housing 12. In one embodiment, the housing 12 includes a motor-powered fan such that the purifying device 10 circulates air through the housing 12. It should be noted that a device other than a motor-powered fan can be used to circulate air through the housing 12 without departing from the scope or spirit of the present invention. The housing 12 also includes a power source (not illustrated), such as a battery or an AC power source, for providing electrical power to the electrical components of the purifying device 10. The purifying device 10 of FIG. 2 includes a user interface 18, which, in the illustrated embodiment, includes a control pad of pressable buttons. Those skilled in the art will recognize that a user interface 18 other than the illustrated user interface 18 can be used without departing from the scope or spirit of the present invention. Additionally, it should be noted that the purifying device 10 need not include the user interface 18 to remain within the scope and spirit of the present invention.

Figure 4:
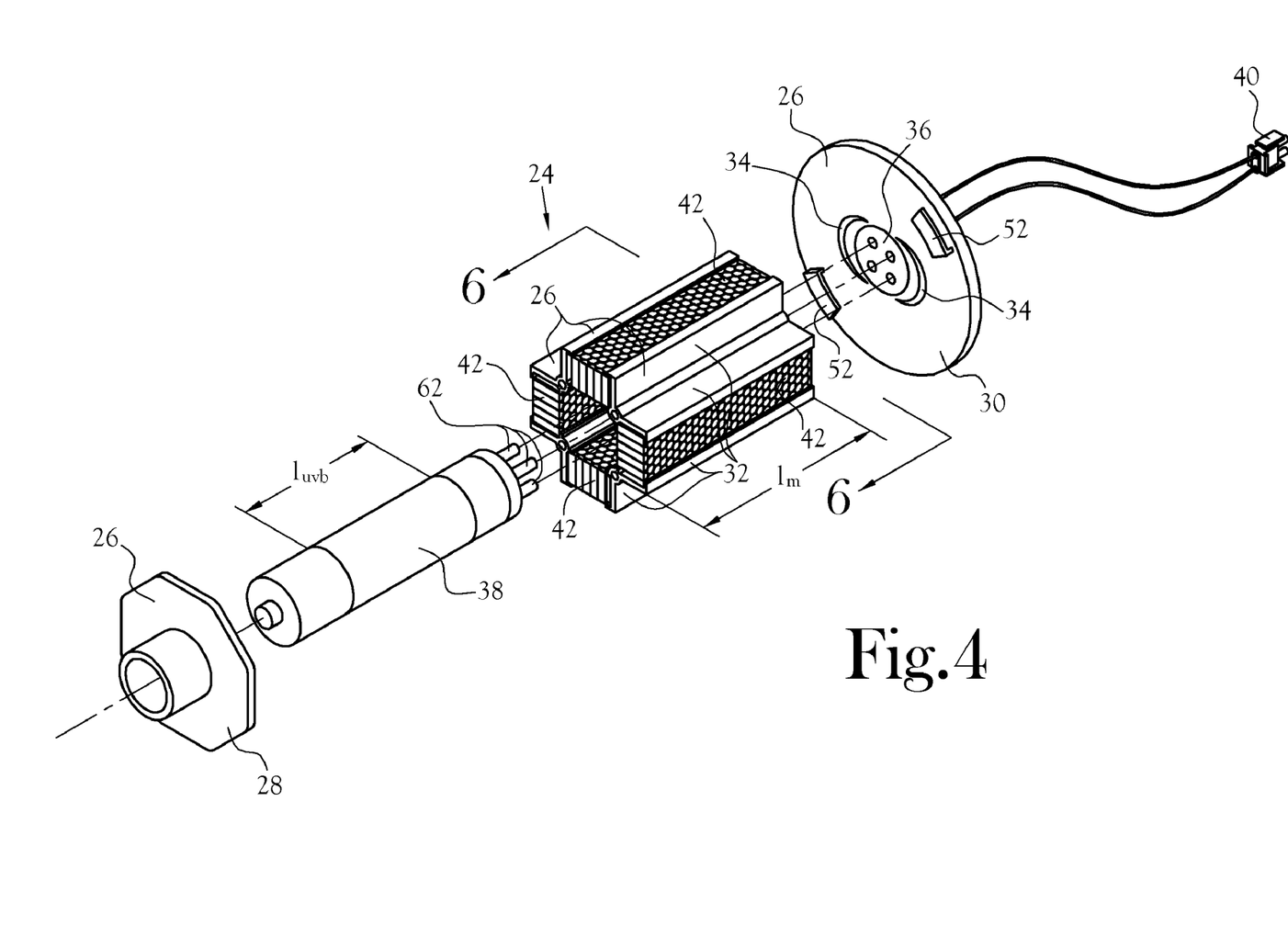
FIG. 4 illustrates one embodiment of the purifying cell of the purifying device in accordance with the various feature of the present invention.

FIG. 4 illustrates one embodiment of a purifying cell 24 in accordance with the various features of the present invention. In the illustrated embodiment, the purifying cell 24 includes a cell frame 26, which includes a cap 28, a base 30, and frame structures 32. The base 30 includes an electrical contact 36, defines a cell air inlet 34, and defines a locking mechanism 52. The purifying cell 24 also includes an ultraviolet (UV) bulb 38, an electrical coupler 40, and a least three matrices 42. The cell frame 26 cooperates with the matrices 42 such that the cell frame 26 and the matrices 42 define a cell cavity that houses the UV bulb 38. The longitudinal length $l_{uvb}$ of the UV bulb 38 is substantially the length $l_m$ of each of matrices 42. The UV bulb 38 radiates ultraviolet light. In one embodiment, the UV bulb 38 is a broad spectrum bulb having high flux between 100 nm and 367 nm. In one embodiment, the UV bulb 38 includes carbide filaments and is made using argon gas with mercury. In one embodiment, the UV bulb 38 emits UVX radiation between 100 nm and 180 nm.

When housed within the cell cavity, the UV bulb 38 is positioned such that its electrical contacts 62 are in electrical communication with the electrical contact 36 at the base 30. The electrical contact 36 is in electrical communication with the electrical coupler 40 such that the UV bulb 38 is in electrical communication with the electrical coupler 40. Additionally, as subsequently illustrated at FIG. 7, the electrical coupler 40 is in electrical communication with the power source of the housing 12 such that the power source provides the UV bulb 38 with operating power. Those skilled in the art will recognize that the UV bulb 38 can be in electrical communication with the electrical coupler 40 by ways other than the electrical contacts 62 and the electrical contact 36 without departing from the scope or spirit of the present invention. For example, in one embodiment, the UV bulb 38 is permanently hardwired directly to the electrical coupler 40 such that the electrical contacts 62 and the electrical contact 36 are not part of the purifying cell 24.

Figure 5:
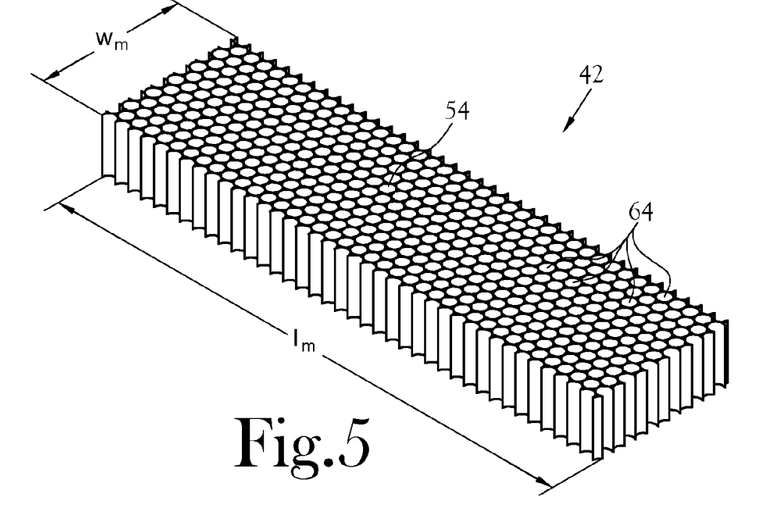
FIG. 5 illustrates one embodiment of one of the matrices of the purifying cell of FIG. 4.

FIG. 5 illustrates one embodiment of one of the matrices 42 in accordance with the various features of the present invention. Each of the matrices 42 includes a plurality of connected substantially parallel hollow elements 64. In the illustrated embodiment, each of the matrices 42 includes a plurality of connected parallel elongated tubular elements. In one embodiment, the matrices 42 are constructed of a rigid plastic, such as a polycarbonate. Each of the matrices 42 includes a width $w_m$ and a length $l_m$. Each of the matrices 42 includes a photocatalytic surface 54 defined by its width $w_m$ and length $l_m$. In one embodiment, the photocatalytic surface 54 includes at least one of titanium dioxide, copper, silver, and rhodium. In one embodiment, the photocatalytic surface 54 is a surface coated with a photocatalytic coating. In one embodiment, the photocatalytic coating includes at least one of titanium dioxide, copper, silver, and rhodium. In one embodiment, the photocatalyst coating is a silica gel that includes one of the above-listed materials. In another embodiment, the photocatalytic coating is a calcium chloride that includes one of the above-listed materials. It should be noted that a photocatalyst other than the specific photocatalysts discussed above can be used for the photocatalytic surface 54 without departing from the scope or spirit of the present invention. Additionally, it should be noted that a structure other than the specific illustrated structure of the matrices 42 can be used without departing from the scope or spirit of the present invention.

Figure 6:
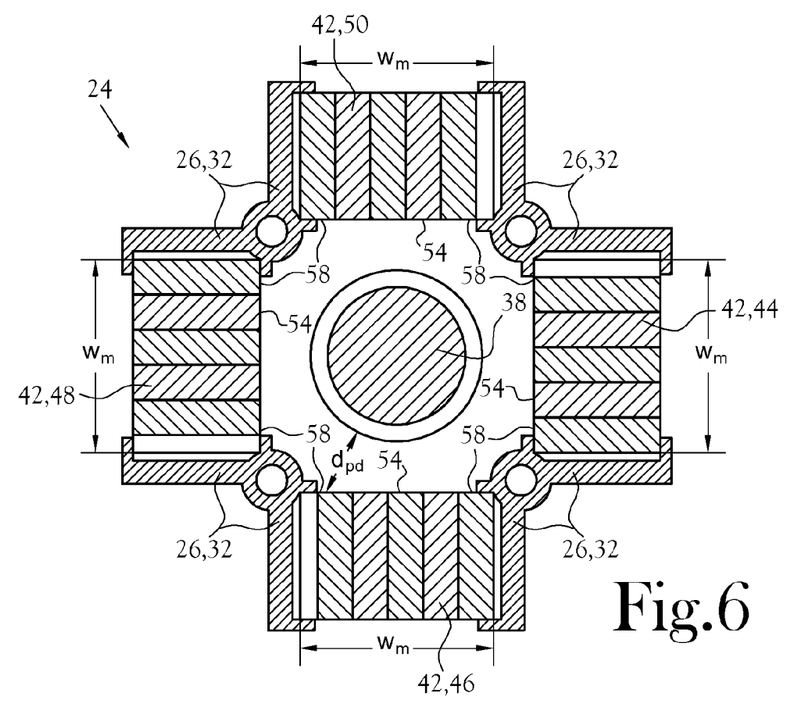
FIG. 6 illustrates a cross-sectional view of the purifying cell of FIG. 4 depicting the configuration of the matrices and the UV bulb of the purifying cell.

FIG. 6 is a cross-sectional view of the purifying cell 24 of FIG. 4 taken at lines 6-6. In the illustrated embodiment, the at least three matrices 42 include four matrices, namely a first matrix 44, a second matrix 46, a third matrix 48, and a fourth matrix 50. The cell frame 26 positions the matrices 42 such that each of the matrices 42 and the UV bulb 38 are substantially longitudinally parallel. Additionally, the frame structures 32 of the cell frame 26 position the matrices 42 such that the matrices 42 substantially encompass the UV bulb 38 along the longitudinal axis of the UV bulb 38. The frame structures 32 also position the matrices 42 such that the photocatalytic surface 54 of each of the matrices 42 is exposed to the ultraviolet light radiating from the UV bulb 38. In the illustrated embodiment, the first matrix 44 and the third matrix 48 are positioned such that the photocatalytic surface 54 of the first matrix 44 is parallel to the photocatalytic surface 54 of the third matrix 48. Additionally, the first matrix 44 is positioned opposite the third matrix 48 with respect to the UV bulb 38. Similarly, the second matrix 46 and the fourth matrix 50 are positioned such that the photocatalytic surface 54 of the second matrix 46 is parallel to the photocatalytic surface 54 of the fourth matrix 50. Additionally, the second matrix 46 is positioned opposite the fourth matrix 50 with respect to the UV bulb 38. Stated differently, each of the matrices 42 is positioned at a quadrant of the UV bulb 38 such that each quadrant of the UV bulb 38 has a corresponding matrix.

Because the UV bulb 38 radiates ultraviolet light, a photocatalytic reaction occurs at the photocatalytic surface 54 of each of the matrices 42. The matrices 42 are positioned such that the potential photocatalytic reaction at the photocatalytic surface 54 of each of the matrices 42 is fully realized. More specifically, each of the matrices 42 is positioned such that the entire photocatalytic surface 54 of each of the matrices 42 is saturated by the radiated ultraviolet light. When the entire photocatalytic surface 54 is saturated, the photocatalytic reaction at the photocatalytic surface 54 is maximized. Stated differently, the potential photocatalytic reaction at the photocatalytic surface 54 is fully realized.

Considering the purifying device 10 of the present invention with respect to a conventional purifying apparatus of the prior art (illustrated at FIG. 1), the above-discussion become more clearly understood. When the width $w_{cpa}$ of each of the first matrix 02 and the second matrix 03 of the conventional apparatus is twice the width $w_m$ of each of the matrices 42 of the purifying cell 24 of the illustrated embodiment, and the matrices of the conventional apparatus and the purifying cell 24 are otherwise identical, the combined area of the photocatalytic surfaces 04 of the conventional apparatus is identical to the combined area of the photocatalytic surfaces 54 of the purifying cell 24. Consequently, the potential photocatalytic reaction at the photocatalytic surfaces 04 of the conventional apparatus is the same as that at the photocatalytic surfaces 54 of the purifying cell 24. Similar to the distance $d_{cpa}$ corresponding to the conventional apparatus (illustrated at FIG. 1), the distance $d_{pd}$ is the distance between the UV bulb 38 and the outermost portions 58 of the photocatalytic surface 54 of each of the matrices 42. And, for the purpose of this discussion, the distance from the ultraviolet bulb 01 of the conventional apparatus to the center of the photocatalytic surface 04 of each of the first matrix 02 and the second matrix 03 is equal to the distance from the UV bulb 38 of the purifying cell 24 to the center of the photocatalytic surface 54 of each of the matrices 42. Because the width $w_m$ of each of the matrices 42 of the purifying cell 24 is less than the width $w_{cpa}$ of the first matrix 02 and the second matrix 03 of the conventional apparatus, the distance $d_{cpa}$ is greater than the distance $d_{pd}$. Consequently, the intensity of the respective radiated ultraviolet light, and consequently the intensity of the respective resulting photocatalytic reaction, at the outermost portions 05 of the photocatalytic surface 04 of the conventional device is less than that at the outermost portions 58 of the photocatalytic surface 54 of each of matrices 42. More specifically, consider the following equation for calculating irradiance:

$$E_2 = \left(\frac{d_1}{d_2}\right)^2 * E_1$$

whereby, $E_1$ is the irradiance at distance $d_1$ from the energy source, and $E_2$ is the irradiance at distance $d_2$ from the energy source.

As an example, the distance $d_{pd}$ from the UV bulb 38 is 0.224 m. Additionally, the distance $d_{cpa}$ from the ultraviolet bulb 01 of the conventional apparatus is 0.295 m, and the irradiance at the distance $d_{cpa}$ is 1.00 lm/m². Assuming the ultraviolet bulb 01 to be identical to the UV bulb 38, and using the equation discussed above, the irradiance at distance $d_{pd}$ is 1.73 lm/m². Stated differently, the irradiance at distance $d_{pd}$ from the UV bulb 38 is 73% greater than the irradiance at distance $d_{cpa}$ from the ultraviolet bulb 01. Because the irradiance at distance $d_{pd}$ is greater than the irradiance at distance $d_{cpa}$, the photocatalytic reaction at distance $d_{pd}$ is greater than the photocatalytic reaction at distance $d_{cpa}$. Consequently, all other factors being identical, the configuration of the matrices 42 of the purifying cell 24, with respect to the UV bulb 38, provides for a photocatalytic reaction having a fully realized potential when the configuration of the first matrix 02 and the second matrix 03 of the conventional apparatus does not.

Considering the above-discussed structure of the purifying cell 24, because the photocatalytic reaction occurs at the photocatalytic surface 54 of each of the matrices 42, the photocatalytic reaction occurs within the cell cavity. The photocatalytic reaction produces a zone of plasma of advanced oxidation products including ozone, hydroperoxides, superoxides, and hydroxyl radicals. Air subjected to the photocatalytic reaction, that is, air in the presence of the photocatalytic reaction, is oxidized and purified of organic contaminants. Consequently, air within the cell cavity is subjected to the photocatalytic reaction and, as a result, is oxidized and purified of organic contaminants.

Figure 7:
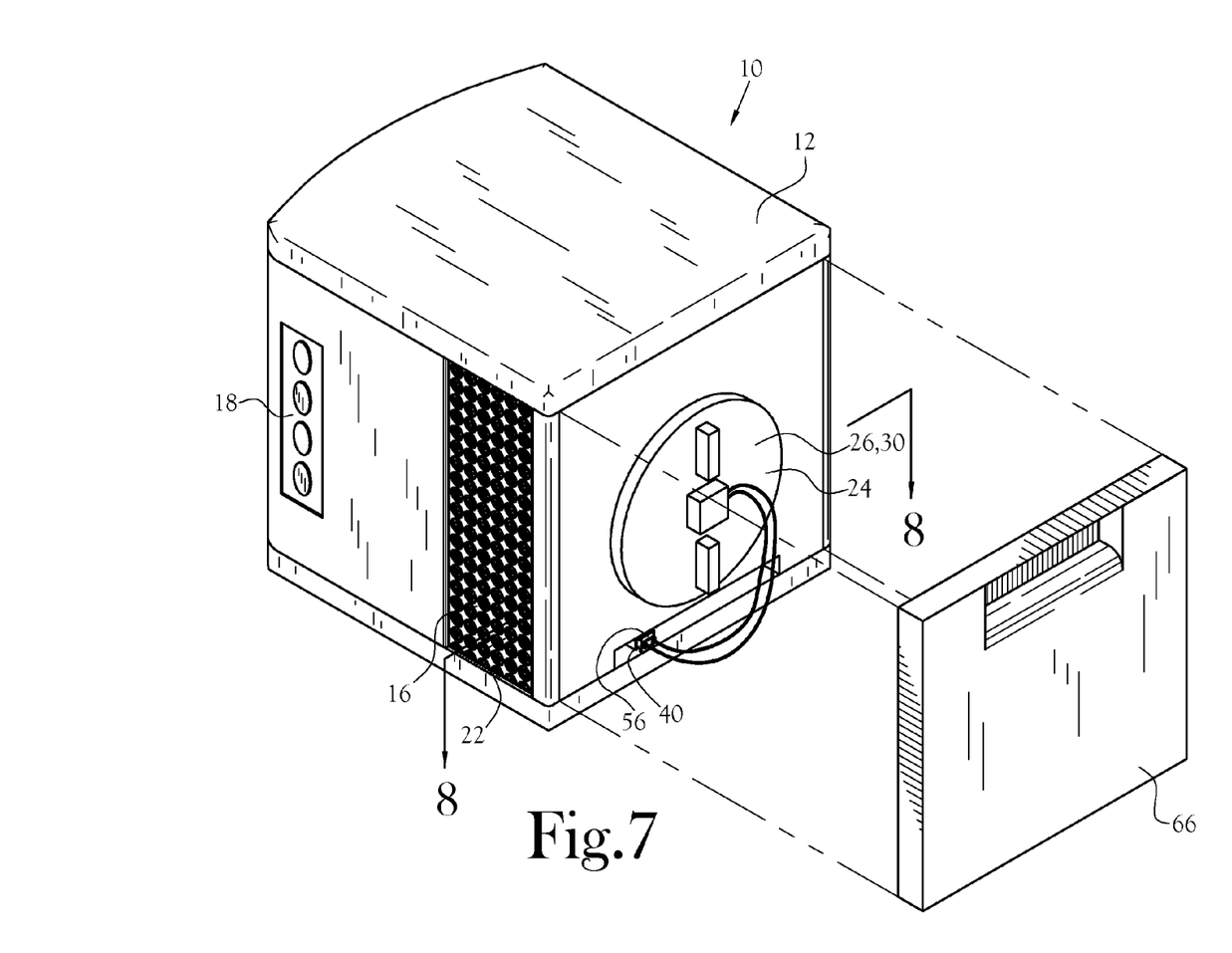
FIG. 7 illustrates the back of the purifying device of FIG. 2.

FIG. 7 illustrates the back of the purifying device 10 of FIG. 2, namely the side of the purifying device 10 opposite the front grill 20. The housing 12 includes a substantially removable back panel 66. In the illustrated embodiment, the back panel 66 is detachable from the remainder of the housing 12. However, the back panel 66 can, for example, merely open by way of hinge members without departing from the scope or spirit of the present invention. The housing 12 receives the purifying cell 24 such that the purifying cell 24 is removeably secured within the housing 12. In the illustrated embodiment, the purifying cell 24 is received such that the cap 28 of the cell frame 26 is disposed toward the air outlet 14, and the base 30 of the cell frame 26 is disposed at the back of the housing 12. Also in the illustrated embodiment, the base 30 is secured to the housing 12 by way of the locking mechanism 52, which cooperates with a corresponding mechanism at the housing 12 such that the purifying cell 24 is removeably secured within the housing 12 by inserting the purifying cell 24 in the housing 12 in accordance with the above-discussion and rotating the base 30 clockwise to the extent that the locking mechanism 52 engages the corresponding mechanism at the housing 12. Additionally, the purify cell 24 is removed from the housing 12 by rotating the base 30 counterclockwise to the extent that the locking mechanism 52 disengages the corresponding mechanism at the housing 12 and removing the purifying cell 24 from the housing 12. The purifying device 10 includes a power connector 56 that is in electrical communication with the above-discussed power source included by the housing 12. The power connector 56 cooperates with the electrical coupler 40 of the purifying cell 24 such that the power connector 56 and the electrical coupler 40 provide a terminable electrical connection between the power source and the UV bulb 38. A terminable electrical connection is one that can be established, disconnected, and reestablished. For example, in the illustrated embodiment, the electrical coupler 40 is a plug, and the power connector 56 is an outlet that receives the electrical coupler 40. When the electrical coupler 40 cooperates with the power connector 56, the power source provides operating power to the UV bulb 38. In the illustrated embodiment, when the purifying cell 24 is secured within the housing 12, the electrical coupler 40 is plugged into the power connector 56.

Considering the above-discussion, the purifying device 10 provides a plug-and-play feature with respect to the purifying cell 24. More specifically, the purifying cell 24 is brought into and out of an electrical connection with the power source included by the housing 12 by plugging and unplugging the electrical coupler 40 into and from the power connector 56. Additionally, the purifying cell 24 is secured within and removed from the housing 12 by rotating the base 30. The plug-and-play feature provides quick and easy removal of the purifying cell 24 for performing tasks such as cleaning or replacing the purifying cell 24.

Figure 8:
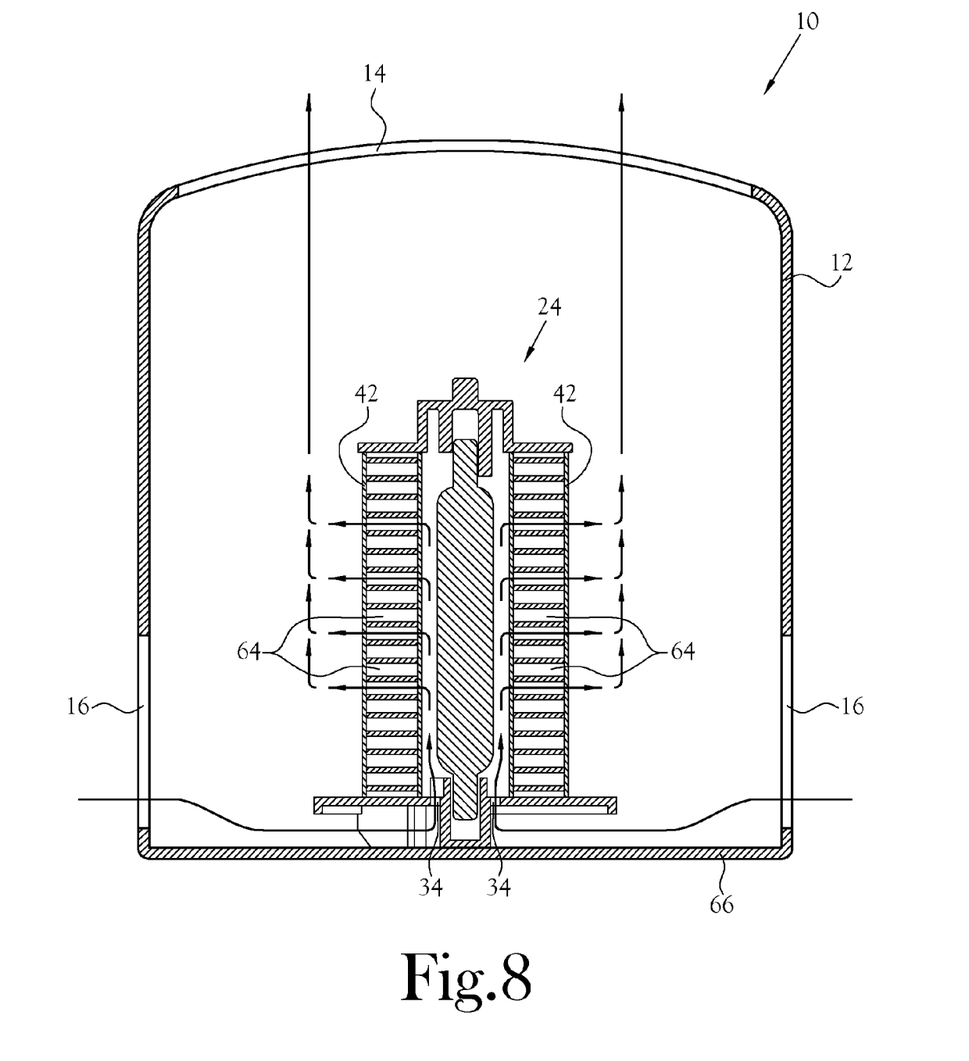
FIG. 8 illustrates a cross-sectional view of the purifying device of FIG. 7 depicting the air flow through the purifying device.

FIG. 8 is a cross-sectional view of the purifying device 10 of FIG. 7 taken at lines 8-8. As discussed above, the purifying device 10 circulates air through the housing 12 by drawing air into the housing 12 by way of the air inlet 16 and forcing air from the housing 12 by way of the air outlet 14. The purifying cell 24 is removeably secured within the housing 12 such that air drawn through the air inlet 16 is channeled to the cell air inlet 34. The air is drawn through the cell air inlet 34 and into the cell cavity. As discussed above, air within the cell cavity is subjected to the photocatalytic reaction. Air that has been subjected to the photocatalytic reaction is drawn from the cell cavity by way of the hollow elements 64 of the matrices 42. Because the matrices 42 substantially encompass the UV bulb 38, air flows from the cell cavity without being trapped in a pocket defined by the cell cavity where air does not circulate. Air drawn through the hollow elements 64 of the matrices 42 is drawn toward the air outlet 14. Stated differently, purified air is drawn from the cell cavity, through the hollow elements 64, and toward the air outlet 14. The purified air is then forced from the housing 12 by way of the air outlet 14. As a result, ambient air containing organic contaminants drawn into the purifying device 10 is purified and forced back into the ambient environment as purified ambient air.

Considering the above-discussion, the purifying device 10 also purifies ambient surfaces. More specifically, the purifying device 10 draws organic contaminants from the surface on which the purify device 10 is placed and oxidizes the contaminants as discussed above.

From the foregoing description, those skilled in the art will recognize that an air and surface purifying device having a purifying cell offering advantages over the prior art has been provided. The purifying cell positions at least three photocatalytic surfaces about a single ultraviolet bulb such that the photocatalytic surfaces substantially encompass the ultraviolet bulb and are saturated by ultraviolet light radiating from the ultraviolet bulb. Because the photocatalytic surfaces are saturated, the potential photocatalytic reaction at the photocatalytic surfaces is fully realized. Stated differently, the realized photocatalytic reaction is maximized. Because the purifying cell maximizes the realized photocatalytic reaction, the purifying cell maximizes the purifying capacity of the photocatalytic surface and, thus, the purifying cell itself.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

The invention claimed is:

1. A purifying cell adapted to be received by a purifying device, said purifying cell comprising:
a cell frame having a plurality of separate frame structures connected together and a cell air inlet, the cell air inlet allowing air to enter said cell frame;
a single ultraviolet bulb radiating ultraviolet light, and
at least three matrices, said connected plurality of frame structures of separate said cell frame holding said matrices about said ultraviolet bulb such that said matrices substantially encompass said ultraviolet bulb, each of said matrices having a photocatalytic surface exposed to the ultraviolet light such that a photocatalytic reaction occurs at the photocatalytic surface of each of said matrices, said cell frame positioning said matrices with respect to said ultraviolet bulb such that the potential photocatalytic reaction at the photocatalytic surface of each of said matrices is fully realized, air entering said cell frame by way of the cell air inlet being subjected to the photocatalytic reaction, air within said cell frame exiting said cell frame by way of said matrices.

2. The purifying cell of claim 1 wherein said ultraviolet bulb is a broad spectrum bulb.

3. The purifying cell of claim 1 wherein said at least three matrices is four matrices.

4. The purifying cell of claim 3 wherein each of said matrices is disposed at a quadrant of said ultraviolet bulb such that one of said matrices is disposed at all quadrants of said ultraviolet bulb.

5. The purifying cell of claim 1 wherein each of said matrices includes a plurality of connected substantially parallel hollow elements.

6. The purifying cell of claim 5 wherein each of said matrices includes a plurality of connected parallel elongated tubular elements.

7. The purifying cell of claim 6 wherein the plurality of connected elongated tubular elements creates a honeycomb-type structure.

8. The purifying cell of claim 1 wherein each of said matrices is constructed of a polycarbonate.

9. The purifying cell of claim 1 wherein the photocatalytic surface of each of said matrices includes a material selected from the group consisting of titanium dioxide, copper, silver, and rhodium.

10. The purifying cell of claim 1 wherein the photocatalytic surface of each of said matrices is a surface coated with a coating including a material selected from the group consisting of titanium dioxide, copper, silver, and rhodium.

11. The purifying cell of claim 10 wherein the coating is a silica gel.

12. The purifying cell of claim 10 wherein the coating is a calcium chloride.

13. The purifying cell of claim 1 wherein the potential photocatalytic reaction at the photocatalytic surface of each of said matrices is fully realized when the ultraviolet light saturates the entire photocatalytic surface.

14. The purifying cell of claim 1 further comprising an electrical coupler in electrical communication with said ultraviolet bulb, said electrical coupler in terminable electrical connection with a power source included by the purifying device.

15. The purifying cell of claim 14 wherein said electrical coupler is a plug that cooperates with a power connector included by the purifying device.

16. A purifying device, said purifying device comprising:
a purifying cell having a single ultraviolet bulb and at least three matrices, the ultraviolet bulb radiating ultraviolet light, each of the matrices having a photocatalytic surface, the matrices being held in position by separate cell frame structures connected together to form a cell cavity to house the ultraviolet bulb, the matrices being disposed about the ultraviolet bulb such that the matrices substantially encompass the ultraviolet bulb and such that the photocatalytic surface of each of the matrices is exposed to the ultraviolet light to the extent that a photocatalytic reaction occurs at the photocatalytic surface of each of the matrices, each of the matrices being disposed such that the distance between the outermost portions of the photocatalytic surface of each of the matrices and the ultraviolet bulb is such that the potential photocatalytic reaction at the photocatalytic surface is fully realized; and a housing receiving said purifying cell, said housing circulating air through said purifying cell such that the air is subjected to the photocatalytic reaction.

17. The purifying device of claim 16 wherein said purifying cell includes four matrices.

18. The purifying device of claim 17 wherein each of the matrices is disposed at a quadrant of the ultraviolet bulb such that one of the matrices is disposed at all quadrants of the ultraviolet bulb.

19. The purifying device of claim 16 wherein the photocatalytic surface of each of the matrices includes a material selected from the group consisting of titanium dioxide, copper, silver, and rhodium.

20. The purifying device of claim 16 wherein the photocatalytic surface of each of the matrices is a surface coated with a coating including a material selected from the group consisting of titanium dioxide, copper, silver, and rhodium.

21. The purifying device of claim 16 wherein the potential photocatalytic reaction at the photocatalytic surface of each of the matrices is fully realized when the ultraviolet light saturates the entire photocatalytic surface.

22. The purifying device of claim 16 wherein said housing includes a fan for circulating air through said purifying cell.

23. The purifying device of claim 16 wherein said purifying cell includes a cell air inlet.

24. The purifying device of claim 23 wherein said housing circulates air through said purifying cell by drawing air into said purifying cell by way of the cell air inlet and from said purifying cell by way of the matrices.

25. The purifying device of claim 16 wherein said purifying cell includes an electrical coupler in electrical communication with the ultraviolet bulb.

26. The purifying device of claim 25 wherein said housing includes a power connector that cooperates with the electrical coupler of said purifying cell such that the ultraviolet bulb is in terminable electrical communication with a power source.

27. A method for purifying ambient air and/or surfaces, said method comprising the steps of:
positioning at least three matrices about an ultraviolet bulb such that the resulting photocatalytic reaction is maximized;
disposing the matrices and the ultraviolet bulb within a housing having an air inlet and an air outlet;
drawing air into the housing by way of the air inlet;
drawing air drawn into the housing proximate the matrices and the ultraviolet bulb such that the air is subjected to the photocatalytic reaction;
forcing air subjected to the photocatalytic reaction from the housing by way of the air outlet; and
wherein said step of positioning includes holding the matrices in position with separate cell frame structures connected together to form a cell cavity about the ultraviolet bulb such that the matrices substantially encompass the ultraviolet bulb and such that a photocatalytic surface of each of the matrices is exposed to ultraviolet light radiated by the ultraviolet bulb to the extent that a photocatalytic reaction occurs at the photocatalytic surface of each of the matrices, the photocatalytic reaction being maximized when the ultraviolet light saturates the photocatalytic surface of each of the matrices.

28. The method of claim 27 wherein said step of disposing includes removeably securing the matrices and the ultraviolet bulb within the housing.

29. The method of claim 27 wherein said step of disposing includes establishing terminable electrical communication between the ultraviolet bulb and a power source included by the housing.

30. The method of claim 27 wherein the housing includes a fan that accomplishes said step of drawing air into the housing, said step of drawing air drawn into the housing proximate the matrices and the ultraviolet bulb, and said step of forcing air subjected to the photocatalytic reaction from the housing.

31. The method of claim 27 further comprising the step of drawing air subjected to the photocatalytic reaction through the matrices.

32. A purifying device, said purifying device comprising:
a purifying cell comprising:
a cell frame defining a plurality of separate frame structures connected together and a cell air inlet, the cell air inlet allowing air to enter said cell frame;
an ultraviolet bulb radiating ultraviolet light;
an electrical coupler in electrical communication with said ultraviolet bulb;
a first matrix having a first photocatalytic surface exposed to the ultraviolet light such that a photocatalytic reaction occurs;
a second matrix having a second photocatalytic surface exposed to the ultraviolet light such that a photocatalytic reaction occurs;
a third matrix having a third photocatalytic surface exposed to the ultraviolet light such that a photocatalytic reaction occurs; and
a fourth matrix having a fourth photocatalytic surface exposed to the ultraviolet light such that a photocatalytic reaction occurs;
whereby said connected plurality of frame structures of said cell frame holds said first matrix, said second matrix, said third matrix, and said fourth matrix about said ultraviolet bulb such that said first matrix, said second matrix, said third matrix, and said fourth matrix substantially encompass said ultraviolet bulb and such that the potential photocatalytic reaction at the first photocatalytic surface, the second photocatalytic surface, the third photocatalytic surface, and the fourth photocatalytic surface is fully realized, air entering said cell frame by way of the cell air inlet being subjected to the combined photocatalytic reaction; and
a housing receiving said purifying cell such that said purifying cell is removeably secured within said housing, said housing defining an air inlet and an air outlet, said housing including a fan drawing ambient air into said housing by way of the air inlet, into said purifying cell by way of the cell air inlet, from the purifying cell by way of said first matrix, said second matrix, said third matrix, and said fourth matrix, and from said housing by way of the air outlet, said housing including a power connector in electrical communication with a power source, said electrical coupler of said purifying cell cooperating with the power connector such that said purifying cell is in terminable electrical communication with the power supply.

* * * * *